(12) United States Patent
Skribek et al.

(10) Patent No.: US 9,790,464 B2
(45) Date of Patent: Oct. 17, 2017

(54) CELL CULTURE MEDIUM (75) Inventors: Henriette Skribek, Gödöllö (HU); László Székely, Värmdö (SE)

(73) Assignee: BioMarker Kft., Gödöllö (HU)

( * ) Notice: Subject to any disclaimer, the term of this patent is extended or adjusted under 35 U.S.C. 154(b) by 470 days.

(21) Appl. No.: 13/497,707

(22) PCT Filed: Sep. 24, 2010

(86) PCT No.: PCT/IB2010/054303
§ 371 (c)(1),
(2), (4) Date: Nov. 12, 2012

(87) PCT Pub. No.: WO2011/036637
PCT Pub. Date: Mar. 31, 2011

(65) Prior Publication Data
US 2013/0071925 A1 Mar. 21, 2013

(30) Foreign Application Priority Data
Sep. 25, 2009 (HU) .................... 0900603

(51) Int. Cl.
*C12N 5/071* (2010.01)
*C12N 5/00* (2006.01)

(52) U.S. Cl.
CPC ......... *C12N 5/0602* (2013.01); *C12N 5/0018* (2013.01); *C12N 2500/84* (2013.01); *C12N 2502/11* (2013.01)

(58) Field of Classification Search
None
See application file for complete search history.

(56) References Cited

U.S. PATENT DOCUMENTS

| | | | | |
|---|---|---|---|---|
| 5,198,357 A * | 3/1993 | Holmovist | ............. | C12N 5/163 435/243 |
| 2003/0153079 A1* | 8/2003 | Fike | ..................... | C12N 5/0018 435/404 |
| 2004/0171089 A1* | 9/2004 | Spruce et al. | ............... | 435/7.23 |
| 2006/0188585 A1 | 8/2006 | Panosyan et al. | | |
| 2010/0003270 A1 | 1/2010 | Kief | | |
| 2012/0052136 A1* | 3/2012 | Rousselot | ............ | A01N 1/0226 424/663 |

OTHER PUBLICATIONS

Schuster et al., Clinical Microbiology Reviews, vol. 15, No. 3, p. 374-389, 2002.*
Chronolab, The Clinical Chemistry—Point of Care, Hemoglobin content of whole blood, http://www.chronolab.com/point-of-care/index.php?option=com_content&view=article&id=446&Itemid=72; accessed Jul. 29, 2013.*
Hochart et al. (British Journal of Haematology, vol. 133, No. 1, p. 62-67, 2006).*
Knudtzon et al. (Scandanavian Journal of Haematology, vol. 22, p. 296-304, 1979).*
Luvoni et al. (Molecular Reproduction and Development, vol. 43, p. 437-443, 1996).*
Ross et al. (Proceedings of the National Academy of Sciences, vol. 71, No. 4, p. 1207-1210, 1974).*
Shandadfar et al. (Stem Cells, vol. 23, p. 1357-1366, 2005).*
Sawant et al. (Asian Journal of Transfusion Science, vol. 1, No. 2, p. 47-51, 2007).*
Deutsch (J Cell Biology, vol. 98 885-93. 1984).*
Alsousou, J. et al.: "The biology of platelet-rich plasma and its application in trauma and orthopaedic surgery: a review of the literature", The Journal of Bone and Joint Surgery. British Volume, Aug. 2009, vol. 91, No. 8, pp. 987-996.
Arosa F.A. et al.: "Red blood cells as modulators of T cell growth and survival", Curr Pharm Des, 2004, vol. 10, pp. 191-201, Abstract.
Flaberg, E. et al.: "Extended Field Laser Confocal Microscopy (EFLCM): combining automated Gigapixel image capture with in silico virtual microscopy", BMC Med Imaging, 2008, vol. 8, pp. 13.
Fonseca, A.M. et al.: "Red blood cells promote survival and cell cycle progression of human peripheral blood T cells independently of CD58/LFA-3 and heme compounds", Cell Immunol, 2003,vol. 224, pp. 17-28.
Fonseca, A.M. et al.: "Red blood cells upregulate cytoprotective proteins and the labile iron pool in dividing human T cells despite a reduction in oxidative stress", Free Radic Biol Med, 2003, vol. 35, pp. 1404-1416.
Fonseca, A.M. et al.: "Red blood cells inhibit activation-induced cell death and oxidative stress in human peripheral blood T lymphocytes", Blood, 2001, vol. 97, pp. 3152-3160.
Gaszling, V.L.W. et al: "Platelet-rich Plasma and Platelet-rich fibrin in human cell culture", Oral Surgery, Oral Medicine, Oral Pathology, Oral Radiology and Endodontics, Mosby-Year Book, St. Louis, MO, US, 2009, vol. 108, No. I, pp. 48-55.
Hochart, H. et al.: "Concentration-dependent roles for heparin in modifying lipopolysaccharide-induced activation of mononuclear cells in whole blood", Thrombosis and Haemostasis, 2008, vol. 99, No. 3, pp. 570-575.
Larsson, R. et al.: "In vitro testing of chemotherapeutic drug combinations in acute myelocytic leukaemia using the fluorometric microculture cytotoxicity assay (FMCA)", Br J Cancer, 1993, vol. 67, pp. 969-974.
Larsson, R. and Nygren, P.: "A rapid fluorometric method for semiautomated determination of cytotoxicity and cellular proliferation of human tumor cell lines in microculture", Anticancer Res, 1989, vol. 9, pp. 1111-1119, Abstract.

(Continued)

*Primary Examiner* — Taeyoon Kim
*Assistant Examiner* — Srikanth Patury
(74) *Attorney, Agent, or Firm* — Jason D. Voight (57) ABSTRACT

The present invention relates to a cell culture medium for culturing human cells comprising an anti-coagulated total blood material wherein the hemoglobin level is from about 8 to about 16 g/dl. More particularly, the invention provides a cell culture medium in which cells present in the blood are disrupted and the insoluble remnants of the lysated cells are removed. Further, the invention provides a method for the preparation of a cell culture medium for culturing human cells, according to the invention.

16 Claims, 11 Drawing Sheets

(56) References Cited

OTHER PUBLICATIONS

Markasz, L. et al.: "Cytotoxic drug sensitivity of Epstein-Barr virus transformed lymphoblastoid B-cells", BMC Cancer, 2006, vol. 6, p. 265.

Markasz, L. et al.: "Effect of frequently used chemotherapeutic drugs on the cytotoxic activity of human natural killer cells", Mol Cancer Ther, 2007, vol. 6, pp. 644-654.

Nagourney, R.A.: "Ex vivo programmed cell death and the prediction of response to chemotherapy", Curr Treat Options Oncol, 2006, vol. 7, pp. 103-110.

Nygren, P. et al.: "Detection of tumor-specific cytotoxic drug activity in vitro using the fluorometric microculture cytotoxicity assay and primary cultures of tumor cells from patients", Int J Cancer, 1994, vol. 56, pp. 715-720.

Nygren, P. et al.: "In vitro drug sensitivity testing of tumor cells from patients with non-Hodgkin's lymphoma using the fluorometric microculture cytotoxicity assay", Ann Oncol, 1994, vol. 5 Suppl 1, pp. 127-131, Abstract.

Porto, B. et al.: "Human red blood cells have an enhancing effect on the relative expansion of CD8+ T lymphocytes in vitro", Cell Prolif, 2001, vol. 34. pp. 359-367.

Samson, D.J. et al.: "Chemotherapy sensitivity and resistance assays: a systematic review", J Clin Oncol, 2004, vol. 22, pp. 3618-3630.

Shay, J.W. and Wright, W.E. "Tissue culture as a hostile environment: identifying conditions for breast cancer progression studies", Cancer Cell, 2007, vol. 12, pp. 100-101.

Mirabet, V. et al: "Human platelet lysate enhances the proliferative activity of cultured human fibroblast-like cells from different tissues", Cell Tissue Banking, Kluwer Academic Publishers, DO, 2007, vol. 9, No. 1, pp. 1-10.

Villman, K. et al.: "Predictive value of in vitro assessment of cytotoxic drug activity in advanced breast cancer", Anticancer Drugs, 2005, vol. 16, pp. 609-615.

\* cited by examiner

Sensitivity of DLBL cells to 30 different cytotoxic drugs as analysed by individual imaging of 500.000 cells from 7680 confocal sections corresponding to 10.31 Gigapixel information live cells - yellow      4 different drug dilutions in triplicates
dead cells - blue

Fig. 2D

| DRUGS | Maximum concentration |
|---|---|
| 5-Flurouracil | 41,66 ug/ml |
| 6-Mercaptopurin | 69,44ug/ml |
| Actinomycin-D | 0,4166ug/ml |
| Asparaginase | 4,166 IU/ml |
| Bevacizumab | 41,66ug/ml |
| Bleomycin | 25 IU/ml |
| Bortezomib | 0,833 ug/ml |
| Carboplatin | 8,33ug/ml |
| Chlorambucil | 83,33ug/ml |
| Cisplatin | 8,33ug/ml |
| Cladribine | 0,833ug/ml |
| Cyclophosphamide | 33,33ug/ml |
| Cytosine-arabinoside | 83,33ug/ml |
| Daunorubicin | 4,166ug/ml |
| Docetaxel | 33,33ug/ml |
| Doxorubicin | 1,66ug/ml |
| Epirubicin | 1,666ug/ml |
| Etoposide | 16,66ug/ml |
| Fludarabine | 20,833 ug/ml |
| Gemcitabin | 50ug/ml |
| Hydroxyurea | 41,66ug/ml |
| Ifosphamide | 33,33ug/ml |
| Methotrexate | 20,833ug/ml |
| MG-132 | 8,33ug/ml |
| Mitomycin C | 0,55 ug/ml |
| Oxaliplatin | 4,166ug/ml |
| Paclitaxel | 5 ug/ml |
| Prednisolone | 16,66ug/ml |
| Streptozotocin | 41,66ug/ml |
| Topotecan | 0,0833ug/ml |
| Vinblastin | 0,833ug/ml |
| Vincristin | 0,4166ug/ml |

| DRUG | SH27 carcinoma | | breast | | SH28 adenocarcinoma | | | lung | AS30 lung adenocarcinoma | |
|---|---|---|---|---|---|---|---|---|---|---|
| | calf | human | pig | calf | human | pig | human | calf | human | calf |
| 5-Fluorouracil | R | R | R | R | R | R | R | R | R | R |
| 6-Mercaptopurin | R | R | R | R | R | R | R | R | R | R |
| Actinomycin-D | + | + | + | + | + | + | + | + | + | + |
| Asparaginase | R | R | R | R | R | R | R | R | R | R |
| Bleomycin | R | R | R | R | R | R | R | R | R | R |
| Bortezomib | R | R | R | R | R | R | R | R | R | R |
| Carboplatin | R | R | R | R | R | R | R | R | R | R |
| Chlorambucil | R | R | R | + | + | + | + | + | + | + |
| Cisplatin | R | R | R | R | R | R | R | R | R | R |
| Cladribine | R | R | R | + | + | R | R | R | R | R |
| Cytosine-arabinoside | R | R | R | R | R | R | R | R | R | R |
| Daunorubicin | R | + | + | + | + | + | + | + | + | + |
| Docetaxel | R | R | R | R | R | R | R | R | R | R |
| Doxorubicin | + | R | R | + | + | + | + | + | + | + |
| Epirubicin | R | R | R | R | R | R | R | R | R | R |
| Etoposide | + | R | R | R | R | R | R | R | R | R |
| Fludarabine | + | + | + | + | + | + | + | + | + | + |
| Gemcitabin | R | R | R | R | R | R | R | R | R | R |
| Hydroxyurea | R | R | R | R | + | R | R | R | R | R |
| Methotrexate | R | R | R | R | R | R | R | R | R | R |
| Mitomycin C | R | R | R | R | R | R | R | R | R | R |
| Oxaliplatin | R | R | R | R | R | R | R | R | R | R |
| Paclitaxel | R | R | R | R | R | R | R | R | R | R |
| Prednisolone | R | R | R | R | + | R | R | R | R | R |
| Topotecan | R | R | R | R | R | R | R | R | R | R |
| Vinblastin | R | R | R | R | R | R | R | R | + | + |
| Vincristin | R | R | R | R | R | R | R | R | R | R |
| Vinorelbine | R | R | R | + | + | + | + | + | ++ | ++ |
| Mix | R | R | R | + | + | + | + | + | + | + |

Fig. 9

CELL CULTURE MEDIUM

This is the national stage of International Application PCT/IB2010/054303, filed Sep. 24, 2010.

The present invention relates to a cell culture medium for culturing human cells comprising an anti-coagulated total blood material wherein the hemoglobin level is from about 8 to about 16 g/dl. More particularly, the invention provides a cell culture medium in which cells present in the blood are disrupted and the insoluble remnants of the lysated cells are removed. Further, the invention provides a method for the preparation of a cell culture medium for culturing human cells, according to the invention.

BACKGROUND OF THE INVENTION

Culturing primary human cell of both normal and malignant origin is a highly desirable but difficult task. The major reason is that most defined culture media were selected to maintain a well-defined specific cell type. These media are although rich in all necessary low molecular weight compounds they often lack critical growth and survival factors. Formulating cell culture media often required that it should be possible to produce in very large quantities for relatively low price. However recent introduction of new microfluidic and automated microscopy techniques make these requirements obsolete.

Primary cultures of normal cells can serve as a source for stem cells for e.g. reconstitution therapy or as ex vivo target for gene delivery in gene therapeutic interventions. Primary cultures of tumor cells may be used for large scale drug sensitivity assays in order to identify suitable anti-cancer drugs for a given patient, test the efficacy of new drug candidates to previously untested tumor types and even in screening of compound libraries to identify new anti-cancer lead candidates.

An important feature of human tumors is that they are continuously evolving and the ideal therapy would require individualized measures perfectly matching the biological features of the tumor. The most straightforward way to achieve this goal is to create a sophisticated albeit highly robust and reliable methods that can measure the response-rate of the tumor to a large variety of therapeutic interventions. These measurements should provide the theoretical underpinning and practical evidence for assay-guided therapy.

Modern day treatment protocols are the results of carefully controlled clinical trials involving thousands of patients over many years. During the last decades, we have witnessed an impressive improvement in patient survival in several forms of leukemias and lymphomas. The development was the most impressive in the case of pediatric leukemias. For these diseases, the careful grouping of patients according different biological markers and prognostic indicators proved to be crucial for selection of the most effective treatment protocols. These protocols heavily rely on the use of relatively old drugs developed in the late 70s and early 80s. Key factor to achieve the greatly improved survival was the rigorous adherence to the standardized treatment protocol. This strategy, albeit very successful in terms of saving lives of pediatric patients, resulted in very aggressive treatment with significant toxicity. Moreover, this strategy left little room for introduction of new drugs. This is particularly unfortunate considering that there are more than sixty licensed drugs with potential anti-cancer effects and there are over hundred novel drugs in the development pipeline of the pharmaceutical industry.

On the other hand, in the case of adult leukemias, the major breakthrough originated from the introduction of novel drugs to treat near terminal patients (e.g. bcr-abl inhibitor Gleevec against CML; proteasome inhibitor Bortezomib against multiple myelomas or monoclonal antibodies such as anti CD20—Rituximab against a variety of B-cell tumors). Despite all effort, a sizable fraction of both pediatric and adult patients does not respond to the therapy or experience repeated relapses. In these cases, selection of individually designed treatment protocol and application of novel drugs would be highly justified The idea to use in vitro drug sensitivity assays to determine the sensitivity profile of leukemic cells was already introduced forty years ago. A variety of techniques were developed that aimed to determine the viability of tumor cells after in vitro culturing with relevant drugs [1]. All assays involve the same four basic steps: i) isolation of cells; ii) incubation of cells with drugs in tissue culture medium; iii) assessment of cell survival; iv) interpretation of the results. Some of these techniques are widely used today such as the ATP conversion, MTT reduction (tetrazolium salt conversion to insoluble formazan) or FMCA (fluorometric microculture cytotoxicity) assays [2, 3] and has been proven to provide clinically useful information about the drug sensitivity of the tumor cells.

The current assays though suffer a number of limitations. One of the most serious limitations is the difficulty to keep primary human tumor cells alive in vitro [4]. Most eukaryotic cells require two types of signals simultaneously for efficient ex vivo expansion: growth-promoting (proliferation) and survival (anti-apoptotic) signals. These signals are conferred as soluble ligands, alternatively ligands that are part of the extracellular matrix or are associated with the surface of neighboring cells. The signaling molecules target receptors on the cells that are specific for any given cell type and differentiation stage. Classical cell culture media normally has to be supplemented by serum or tissue extracts in order to support efficient in vitro cell growth. The regularly used 10% fetal bovine serum provide sufficient amount of PDGF and insulin like growth factors to support the expansion of primary fibroblasts and mesenchymal stem cells. Most primary cells, however, require the addition of extra growth factors. The generation of in vitro adapted cell lines is achieved by selection of rare genetic variants that are able to expand solely with the help of PDGF and IGF like molecules. Both normal and tumor cells of the lymphoid/myeloid lineage require extra growth/survival factors for in vitro expansion. Importantly shortage of survival factors sensitizes the cells for cytotoxic drug effects creating an undesirable overestimation of the drug efficacy in short term in vitro survival assays. The present day assays often require a sizable amount of tumor cells and they are often very labor-intensive. Due to the limited number of measurements they can carry out, most assays do not allow testing of large number of drugs in different concentrations in repeated series. Most assays have low information content and regularly restricted to single measurement readout (e.g. estimation of the number of live cells per sample).

Moreover, not all drugs are suited for the conventional in vitro survival assays. Some of them, such as the highly fluorescent anthracyclines, are incompatible with direct fluorescence readout technology. Despite of these shortcomings short-term survival assays already started to deliver clinically important information [1, 5-7].

Until recently, in vitro assays were regarded as an unreliable approach to predict in vivo drug response. These sentiments stemmed from the unimpressive results of in vitro clonogenic assays of ovarium carcinomas. However, the perspective of in vitro assays is shifting in the prediction of drug response, as is evidenced by in a recent review [8] of most of the work, concerning ex vivo drug sensitivity assays, published through the 1980s—"reflected the prevailing view of cancer as a disease of dysregulated cell proliferation. The description of apoptosis and programmed cell death, fundamental to our modern understanding of human tumor biology, did not occur until well after the heyday of in vitro chemosensitivity testing. By incorporating the modern tenets of carcinogenesis associated with perturbations in cell survival we can now re-examine laboratory assays of drug response in the context of drug-induced programmed cell death."

The main reason for failures was that most cell culture media were developed by starting out from chemically defined simple solutions and gradually adding different serum or tissue extracts until the test cells showed satisfactory survival and proliferation. It is clear now that new approaches are necessary to revive in vitro chemosensitivity testing, to allow finding the optimal, and preferably personalized, treatment for cancer.

The rapid development of digital imaging, the recent breakthroughs in microscopy and laser optics and new methods in lab automation and microfluidics brought this idealized method within reach. We have shown that it is now possible to build and program automated intelligent confocal microscopes that can test the effect of all presently available anti-cancer drugs on primary tumor cells isolated from volumes as small as 1 ml blood, bone marrow, ascites fluid and pleural effusion. The ability to manufacture 384 well drug plates using preprogrammed fluid dispensing robots allows testing of a large number of drugs in different concentrations, alone or in different combinations. Sophisticated fluorescence labeling techniques reveal multiple vital parameters of the drug treated tumor cells such as viability, cell cycle distribution, metabolic activity and motility.

The only missing element for comprehensive in vitro drug testing is a reliable, efficient culturing medium that preserves the original in vivo conditions as much as possible to help identify the best possible treatment regimen.

To satisfy this need, we have completely re-designed the culture conditions for primary tumor cells. In our approach, we preserve the original in vivo conditions as much as possible. The theoretical basis of our new cell culture medium relies on the following previous observations: primary human lymphocytes, highly apoptosis prone when explanted into cell culture media in the absence of extra growth factors, can survive in total blood for several days [9-12] even if it undergoes partial hemolysis [13]. However, none of these prior art discloses or even suggests the feasibility whole blood as the basis of culture medium for culturing human cells.

Accordingly, the present invention provides a cell culture medium for culturing human cells comprising an anti-coagulated total blood material wherein the hemoglobin level is from about 8 to about 16 g/dl.

In another embodiment, the invention provides a cell culture medium, wherein the cells present in the blood are disrupted and the insoluble remnants of the lysated cells are removed.

In a further embodiment, the invention provides a cell culture medium, wherein the blood is of mammalian origin. In a specific embodiment, the invention provides a cell culture medium, wherein the blood is of human origin.

In another embodiment, the invention provides a cell culture medium, wherein the ion content of the medium is restored to match that of the extracellular fraction of total blood starting material.

In a further embodiment, the invention provides a cell culture medium, wherein the low molecular weight (<3000 Dalton) nutrient content and/or composition is essentially the same as that of a conventional cell culture medium selected preferably form the group consisting of RPMI, DMEM, and IMDM.

In another embodiment, the invention provides a cell culture medium, wherein the reducing capacity of the medium is restored by addition of reduced glutathione.

In a further aspect, the invention provides the use of a cell culture medium according to the invention for culturing human cells.

In a further aspect, the invention provides a method for the preparation of a cell culture medium for culturing human cells, comprising
 (a) providing anti-coagulated mammalian blood as starting material;
 (b) mechanically disrupting the cells present in the blood;
 (c) removing the insoluble remnants of the lysated cells.

In another embodiment, the invention provides a method, wherein the mechanical disruption of the cells is achieved by freezing the total blood or by ultrasound, electric blade homogenizer or French press.

In another embodiment, the invention provides a method, wherein removal of the insoluble remnants of the lysated cells is achieved by ultracentrifugation or mechanical filtration.

In another embodiment, the invention provides a method, wherein the low molecular weight (<3000 Dalton) content and/or composition of the medium is adjusted by dialysis against conventional cell culture medium selected preferably form the group consisting of RPMI, DMEM, and IMDM.

In another embodiment, the invention provides a method, wherein the reducing capacity of the medium is restored by addition of reduced glutathione.

In a further aspect, the invention provides a cell culture medium for culturing human cells, obtainable by the method according to the invention.

DETAILED DESCRIPTION OF THE INVENTION

The methods of establishment of primary cell cultures from human tissues suffer number of limitations. In vitro explanted primary cells require an environment that has similar physico-chemical properties as well as an array of biological signals that are similar to the in vivo milieu.

The present invention embodies a new cell culture medium that maintains the correct ion, osmotic, and redox conditions of the total blood along with fully preserved growth and survival factor flora. The new cell culture medium is based on total blood extract that contains all macromolecular components of blood in addition to all small molecular nutrients of conventional tissue culture medium but lacks the membrane fraction of the red blood cells. We claim that the new medium is superior to conventional media in supporting the survival of primary human cells of normal and malignant origin. It is particularly suitable for drug sensitivity testing of freshly explanted human tumor cells thus creating the basis for a new technological platform for determination of cytotoxic drug sensitivity profiles of individual patients. Short-term drug sensitivity assay may pave the way for individualized assay guided therapy of cancer. The optical properties of the new medium permit fluorescence high content analysis (HCA) evaluation of the treated cells. The medium also quenches the autofluorescence of most of the commonly used drugs. The medium is also well suited for high throughput screening of large chemical of biological compound libraries or large scale toxicological testing on primary human cells.

We have therefore developed, based on our empiric data, a new cell culture medium that unites the cell survival promoting components with the nutritional values of cell culture media in the correct ion and redox environment. We have tested the medium on a large series of cell lines of different origin, as well as on primary tumors from ascites fluids or pleural effusions accompanying ovarium, breast, colon, rectum, pancreas and bladder carcinomas and on isolated tumor cells from AML, ALL, CLL, body cavity lymphomas, Hodgkin and post-transplant lymphomas. When comparing the new medium with conventional cell culture media, we have regularly found improved survival and decreased cytotoxic drug sensitivity of primary tumor cells. Our novel cell culture medium permits extended survival of human tumor cells in vitro. Using the new culture medium it is now possible to carry out assays that can determine the drug sensitivity pattern of freshly isolated primary tumor cells from patients suffering from leukemias, lymphomas or advanced disseminated carcinomas.

The present invention comprises a procedure that converts human (or animal) whole blood into a cell culture medium that support the ex vivo survival of primary human cells and compatible with various fluorescence imaging techniques for viability determination and measurement of various physiological functions. It is based on mechanical lysis of the undiluted anti-coagulated blood, removal of red blood cell ghosts, restoration of the correct ion content, equilibration with low molecular weight nutrients and restoration of reducing conditions. The final product can be immediately used in short-term assays or stored in frozen form over a long period of time.

Although lysates of total blood is a frequent additive of certain bacterial culture media such as blood agar, it is not used in culturing of human or other mammalian cells. The current invention concerns the development of eukaryotic cell culture medium, primarily for ex vivo culturing of human tumor cells/stem cells. The chemical composition of bacterial and eukaryotic media is so much different that mammalian cells do not survive in that bacterial medium. Since the whole blood is only a specific additive in those media, the hemoglobin concentration is well below the level which characterizes the present cell culture medium.

Accordingly, the present invention provides a cell culture medium for culturing human cells comprising an anti-coagulated total blood material wherein the hemoglobin level is from about 8 to about 16 g/dl. Given the fact that the present medium is essentially composed of the whole blood starting material, the high hemoglobin content is the result of the lysis of red blood cells during the processing of the whole blood material. More particularly, the hemoglobin concentration of the cell culture medium according the invention is from about 10 to about 14 g/dl, preferably from about 11 to about 12 g/dl, and even more preferably about 11 g/dl.

Another advantageous characteristic of the cell culture medium according to the invention is that although the medium per see is not transparent, high throughput microscopic imaging can be efficiently carried out. According to the state of the art, high sensitivity fluorescence measurements of cell viability are not compatible with several commonly used anticancer drugs (e.g. epirubicin, daunorubicin, doxorubicin) with high endogenous autofluorescence properties using conventional cell culture media. We showed that using blood extract based culture medium the disturbing autofluorescence is efficiently quenched. The present cell culture medium is not transparent, having the characteristic color of the blood, said high throughput microscopic imaging can be carried out using inverted microscope systems where the cells are collected at the bottom of the culture vessels.

A main feature of the cell culture medium according to the invention is that the cellular components of the whole blood are eliminated as such, but the materials contained said cellular components are retained in the cell culture medium. This is achieved by the disruption of the cells present in the blood and the removal of the insoluble remnants of the lysated cells. Such disruption and removal can be carried out by any suitable means available to the person skilled in the art.

The present invention also provides a method for the preparation of a cell culture medium for culturing human cells, comprising
  (a) providing anti-coagulated mammalian blood as starting material;
  (b) mechanically disrupting the cells present in the blood;
  (c) removing the insoluble remnants of the lysated cells.

En exemplary protocol for the method of the invention is given in Example 1, however, the person skilled in the art will be readily capable to substitute different procedures to achieve essentially the same results as given in the above steps. For example, mechanical disruption of the cells can be achieved, as non-limiting examples, by freezing the total blood or by ultrasound, electric blade homogenizer or French press. The optimization of the suitable parameters for each of these techniques is also apparent for the person skilled in the art. Similarly, after the cell disruption, removal of the cell ghosts can be done by using one or more of several different state of the art techniques. Non-limiting examples are ultracentrifugation or mechanical filtration.

As we detailed above, one of the main objective to be achieved by providing the cell culture medium according to the invention is to ensure optimal culturing conditions for human cells ex vivo. It is apparent that human blood will provide the closest possible match for human cell culturing. Accordingly, as far as it is feasible and possible, the blood base material for the present cell culture medium is of human origin. Alternatively, when the desired culturing protocol allows it or calls for, the human blood based medium can be substituted for by a cell culture medium according to the invention that is based on the whole blood of another mammalian species, preferably of bovine or porcine origin.

As it is apparent for the person skilled in the art, the disruption of the cellular components of the whole blood will release their content into the medium, altering the original composition of the whole blood. In preferred embodiments, therefore, it is also may be desired to modify the composition of the resulting medium to more closely match the composition of the starting material, i.e. the whole blood. Or alternatively, to make its composition similar to the composition of cell culture media conventionally used in the field. The person skilled in the art will be readily able to determine what type of adjustment is the most suitable for the intended use of the cell culture medium according to the invention.

Accordingly, in a specific embodiment, the ion content of the medium is restored to match that of the extracellular fraction of total blood starting material. In another specific embodiment, the reducing capacity of the medium is restored by addition of reduced glutathione. Further, in another specific embodiment, the low molecular weight (<3000 Dalton) nutrient content and/or composition is essentially the same as that of a conventional cell culture medium selected preferably form the group consisting of RPMI, DMEM, and IMDM. The person skilled in the art will be able the select from the available state of the art techniques to achieve any of these modifications, or any other modification that he deems appropriate. Non-limiting examples are given below in the Examples.

DESCRIPTION OF THE FIGURES

FIG. 2: A: Design of basic 384-well plate for testing 30 drugs. B: Primary human ovarian carcinoma cells after 7 days culturing in blood extract based medium (Phase contrast—nuclear staining with live cell compatible Hoechst 33342). C: Sensitivity of DLBL cells to 30 different drugs as analysed by individual imaging of 500.000 cells from 7680 confocal sections. D: Maximum concentrations of the drugs used.

EXAMPLE 1: PRODUCTION OF TOTAL HUMAN BLOOD EXTRACT

Figure 1:
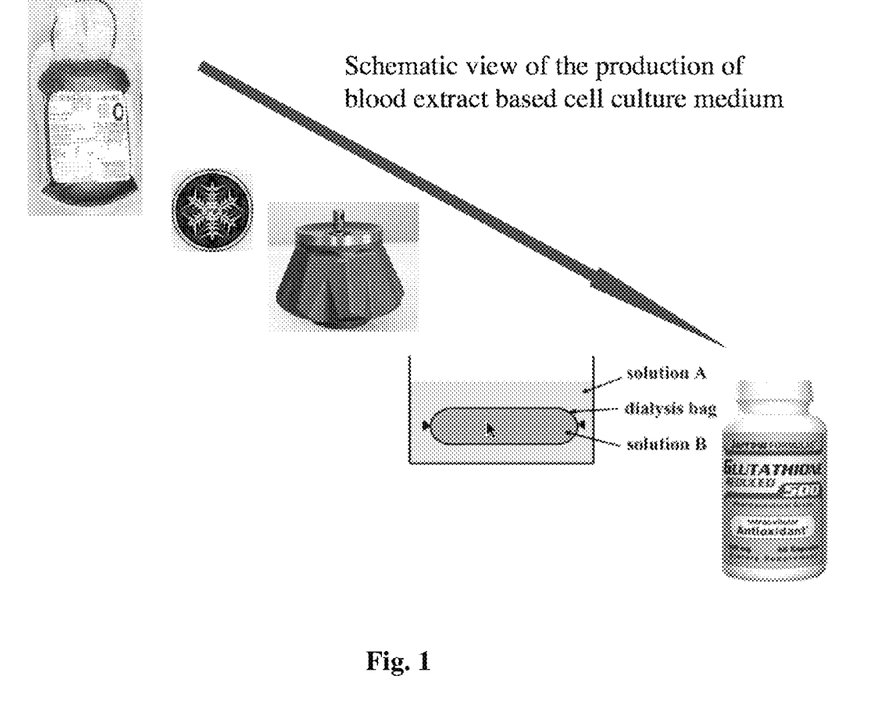
FIG. 1: Schematic view of the production of blood extract based cell culture medium

Human blood from a healthy donor is obtained by venopuncture. Alternatively animal blood (preferentially bovine or porcine origin) is freshly collected under sterile conditions during the time of slaughter. Coagulation is prevented by adding 100 IE Heparin per ml to the collecting bag. Subsequently the red blood cells are lysed in order to release the intracellular content of the red blood cells into the plasma. In an optimal embodiment of the formulation the lysis is carried out by freezing the anti-coagulated blood to −20° C. in 50 ml aliquots, in controlled temperature freezing device to achieve the optimal and even disruption of red blood cell membranes by the help of microscopic ice crystal formation. Subsequently the frozen blood is stored at −80° C. until further processing. To correct the ion content changes, resulted by the hemolysis, and to supply small molecular weight nutrients, the lysed blood is dialysed against excess volume of cell culture medium such as Dulbeccos modified Eagle medium (DMEM—D6546, Sigma-Aldrich Company) or Iscoves modified DMEM (IMDM). In an optimal embodiment of the formulation the 50 ml frozen blood, kept in Falcon plastic tube, is thawed in a 37° C. water bath. The thawed blood lysate is filled into a rehydrated Cellu SepH1 dialysis bag (0310-46, M.S.E. Micron Separation Europe, Belgium—size exclusion limit 3500D). The bag is closed under mild (1.2-1.4 bar) extra pressure over the normal atmospheric pressure to remove air bubbles and to prevent further volume expansion. The dialysis is carried out in the dark, for 24 hours, at 4° C. against twenty fold excess fluid under constant magnetic stirring. The red blood cell membrane ghosts are removed by centrifugation. In an optimal embodiment of the formulation the centrifugation is carried out a through a microporous silica matrix equilibrated with the medium that was used for the dialysis. The proper removal of the ghosts is monitored and documented by taking 10 microliter samples from every 50 ml filtered lysates and checked using automated digital phase contrast microscopy. In order to create a proper redox milieu, the particle free blood lysate is supplemented with an extra reducing agent. In an optimal embodiment of the formulation the agent is 0.5 mM reduced glutathione (G6013, Sigma-Aldrich Company). Subsequently the lysate is vacuum filtered through a nitrocellulose membrane (Corning 431153, Corning Inc.) with 0.22 micrometer pore size and, immediately after the last filtration step flash frozen in liquid nitrogen, in 3 ml aliquots. The frozen aliquots are stored at −80 C until use in the biological assays. See FIG. 1 for the schematic overview of the procedure.

EXAMPLE 2: VIABILITY ASSAY OF DRUG TREATED PRIMARY HUMAN TUMOR CELLS

Total blood lysate based cell culture medium is particularly suitable for testing the drug sensitivity of primary human cells that grow in suspension form, using short term in vitro survival assays. For this assays the cells are purified from peripheral blood, bone marrow or body cavity (peritoneal or pleural) effusions using Ficoll gradient centrifugation. In the regular setup of the assay, ten ml body fluid is treated with 100 IE/ml heparin in order to prevent coagulation. The fluid is overlayed on 5 ml LymphoprepR (Frezenius Kabi Norge AS) cushion and centrifuged for 10 minutes at 2500 rpm.

The cells from the gradient interphase are collected and washed with pre-warmed cell culture medium containing 20% human serum. The quality and tumor cell content of the sample is checked and documented using phase contrast microscopy. If the tumor cell count is below 70% the cells are further purified by negative selection using an appropriate Dynabead cocktails reacting with the contaminating normal (e.g. inflammatory) cells. The identity of the tumor cells is verified in independent assays using immunohistochemical markers. For example carcinoma cells in body cavity effusions are identified on Cytospin slides with immunofluorescence staining against pan-cytokeratin antibodies. The presence of T, B, plasma-, NK cells, granulocytes and macrophages/monocytes is routinely tested using for example anti CD3, CD4, CD8, CD19, Ig, CD56, Mac1 antibodies. The drug sensitivity of the tumor cells are tested on 384 well plates.

Figure 2A:
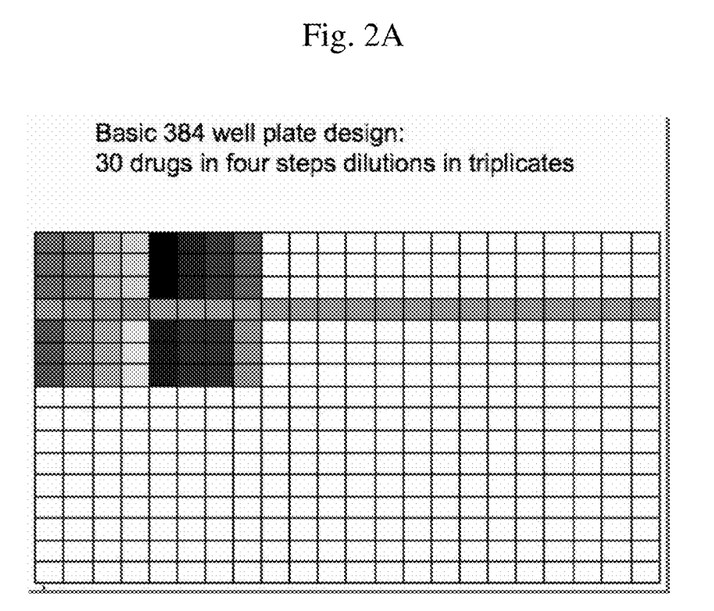
Figure 2B:
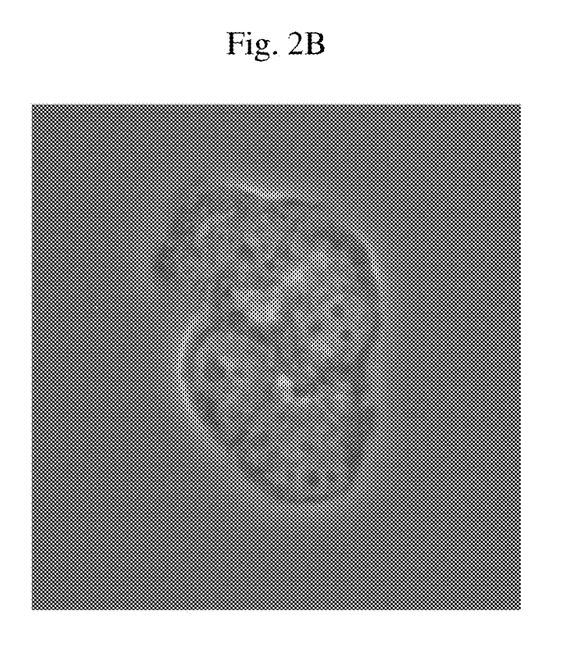
Figure 2C:
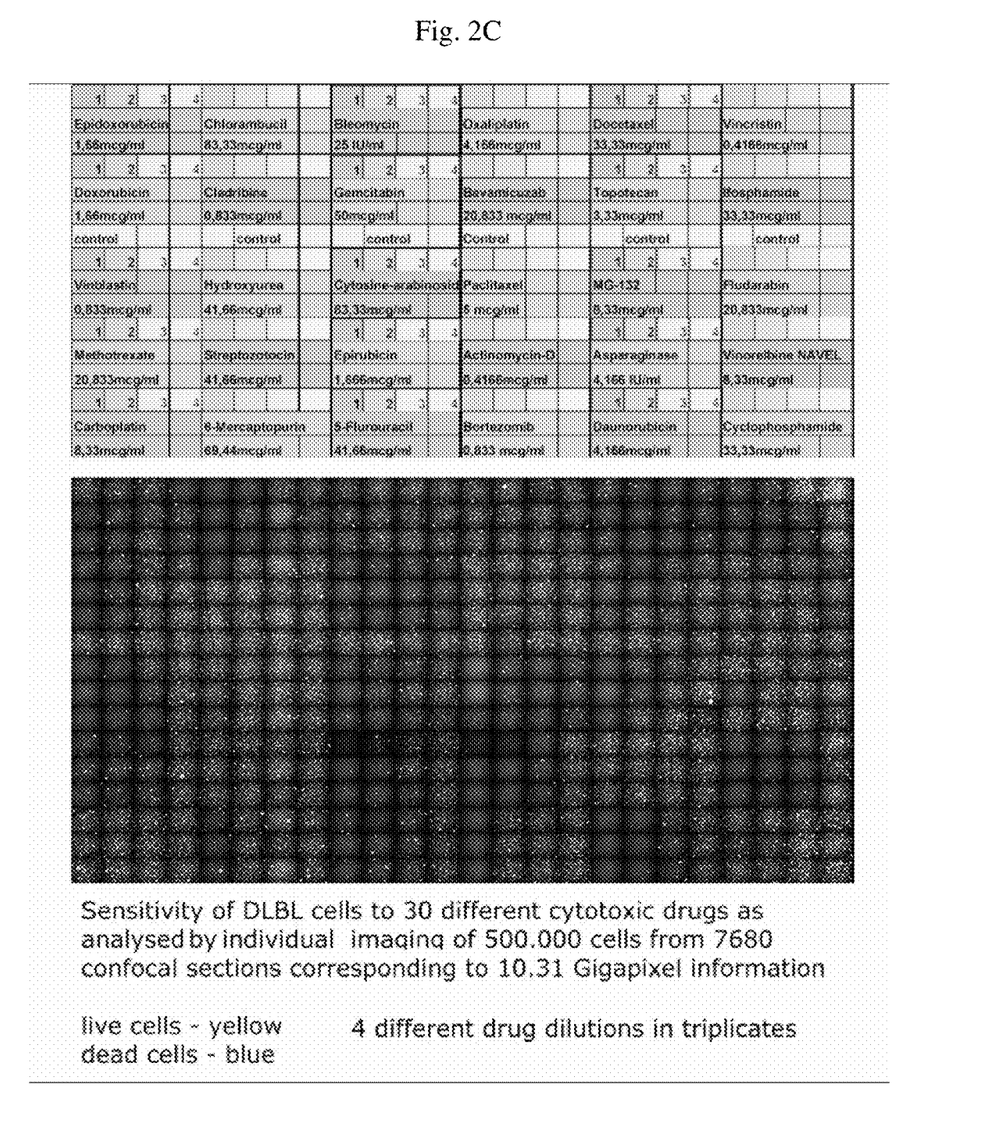
Figure 2D:
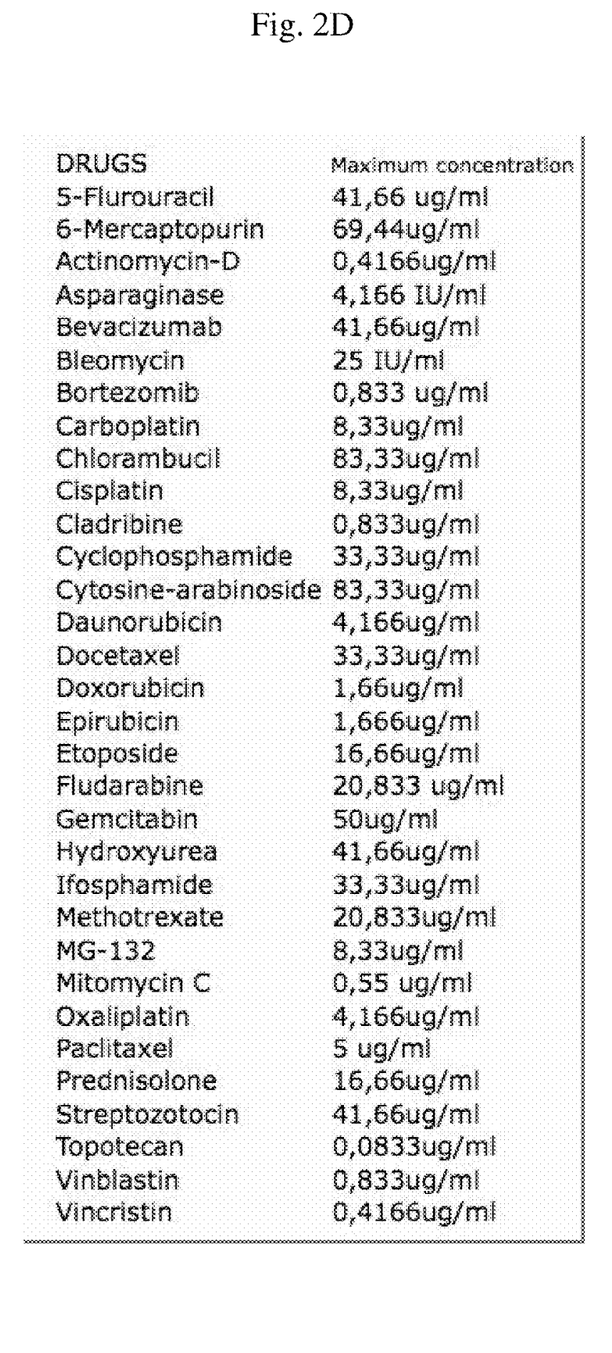

The pre-printed 384-well drug plates are produced using a Biomek 2000 laboratory robot equipped with flat end stainless steal metal pins with 50 nanoliter replica volumes. The master-plates are created by serially diluting the drug stock solutions using combination of single tip and 8 tip mode of the robot. In a typical set-up we handle 30 different drugs in 4 different dilution series (regularly 1× 5× 25× 125× diluted from the stock, in 50% DMSO/PBS) in triplicates along with 24 control wells. An example of a drug series with the highest employed drug concentrations is shown in the table on FIG. 2. The drug concentrations are selected considering the pharmacokinetic AUC values for human subjects as established in clinical studies [14, 15]. When it is necessary, active metabolites are used instead of the original inactive pro-drug (e.g. 4-OH cyclophosphamide).

Figure 3:
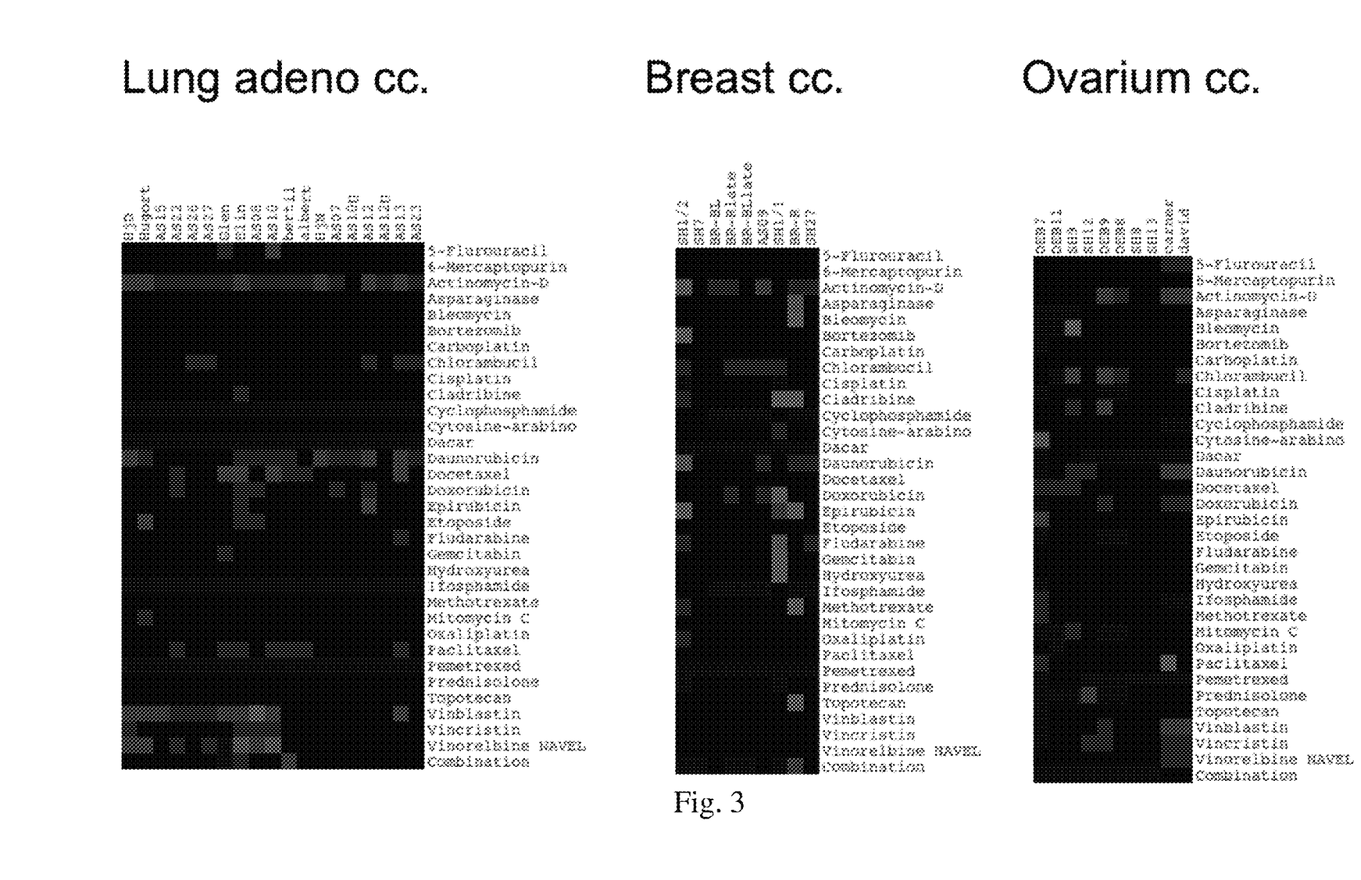
FIG. 3: Drug sensitivity pattern of 38 different primary human carcinoma cells isolated directly from pleural effusion or ascites fluids and tested in a three days survival assay in human blood extract based medium as shown in FIG. 2. (The 5 step intensity scale of the heat map corresponds to 50% survival rate at the given drug dilution. Black: more than 50% survival at the highest drug concentration, highest intensity red less than 50% survival at the highest drug dilution).
Figure 4:
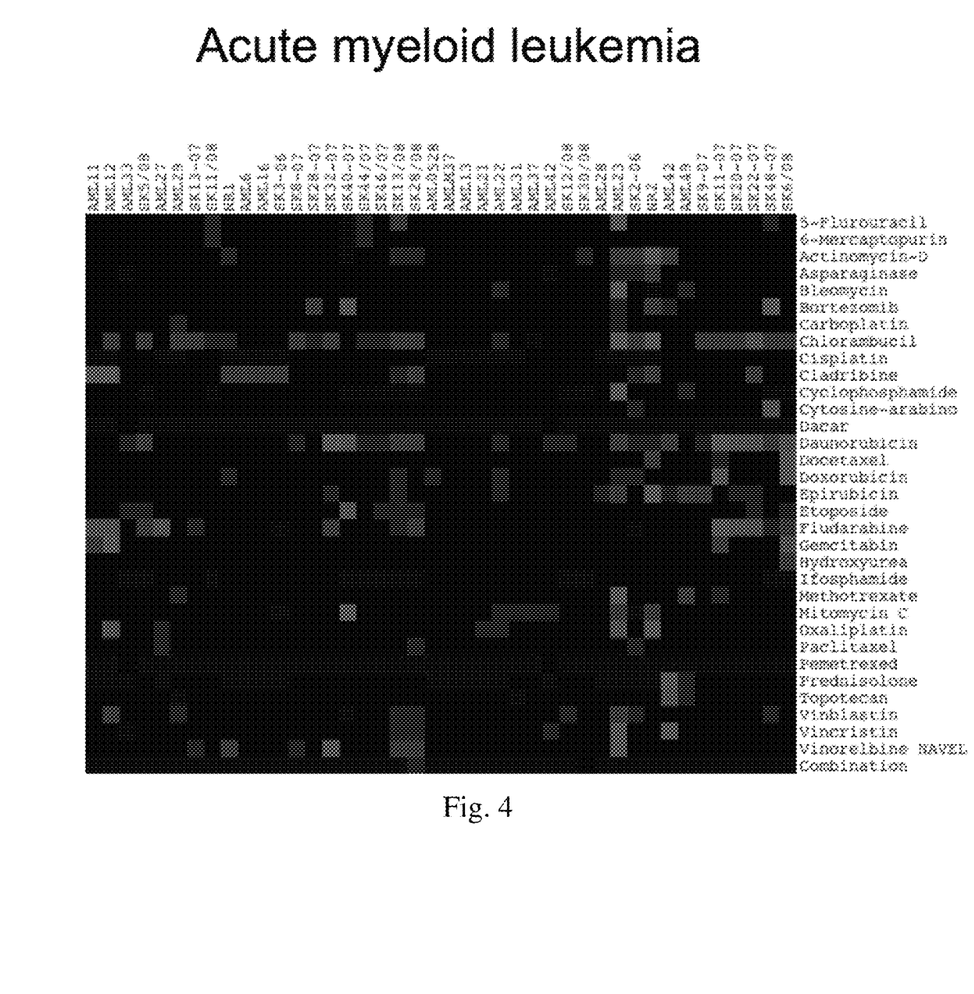
FIG. 4: Drug sensitivity pattern of 42 different primary Acute Myeloid Leukemia cells isolated directly from the peripheral blood of patients and tested in a three days survival assay in human blood extract based medium as shown in FIG. 2. (The 5 step intensity scale of the heat map corresponds to 50% survival rate at the given drug dilution. Black: more than 50% survival at the highest drug concentration, highest intensity red less than 50% survival at the highest drug dilution).
Figure 5:
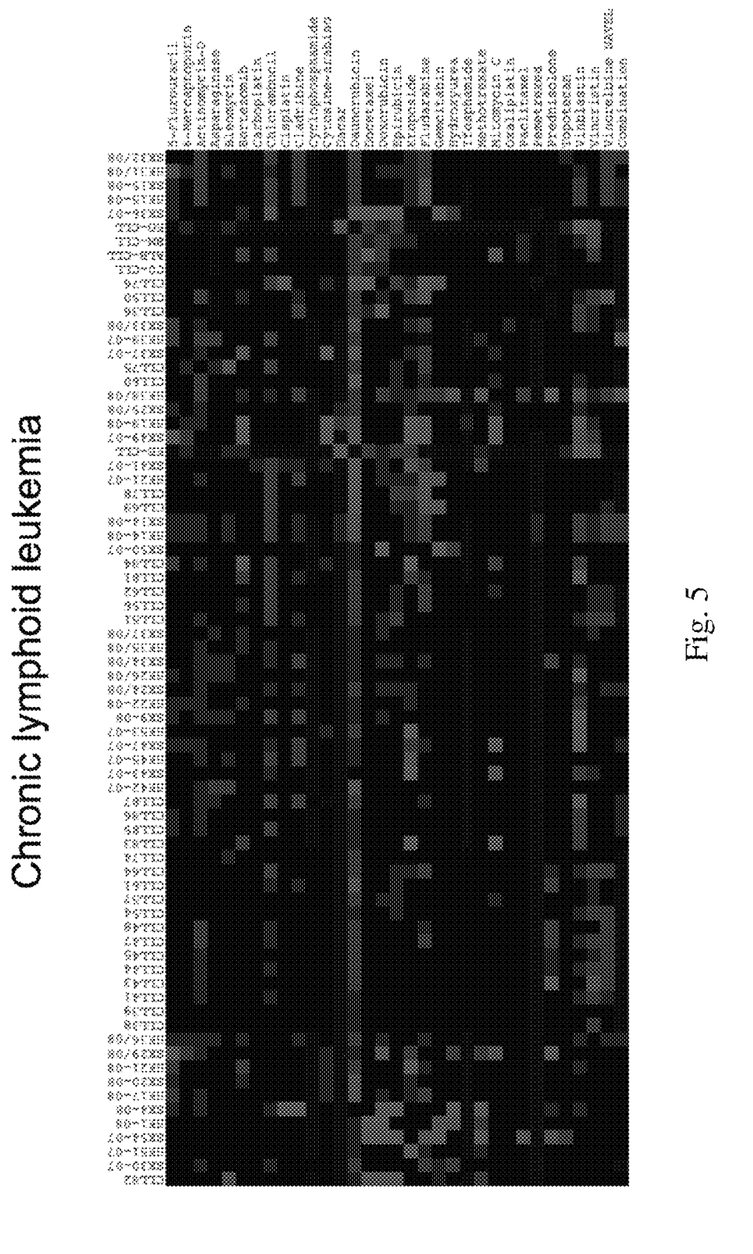
FIG. 5: Drug sensitivity pattern of 74 different primary Chronic Lymphoid Leukemia cells isolated directly from the peripheral blood of patients and tested in a three days survival assay in human blood extract based medium as shown in FIG. 2. (The 5 step intensity scale of the heat map corresponds to 50% survival rate at the given drug dilution. Black: more than 50% survival at the highest drug concentration, highest intensity red less than 50% survival at the highest drug dilution).
Figure 6:
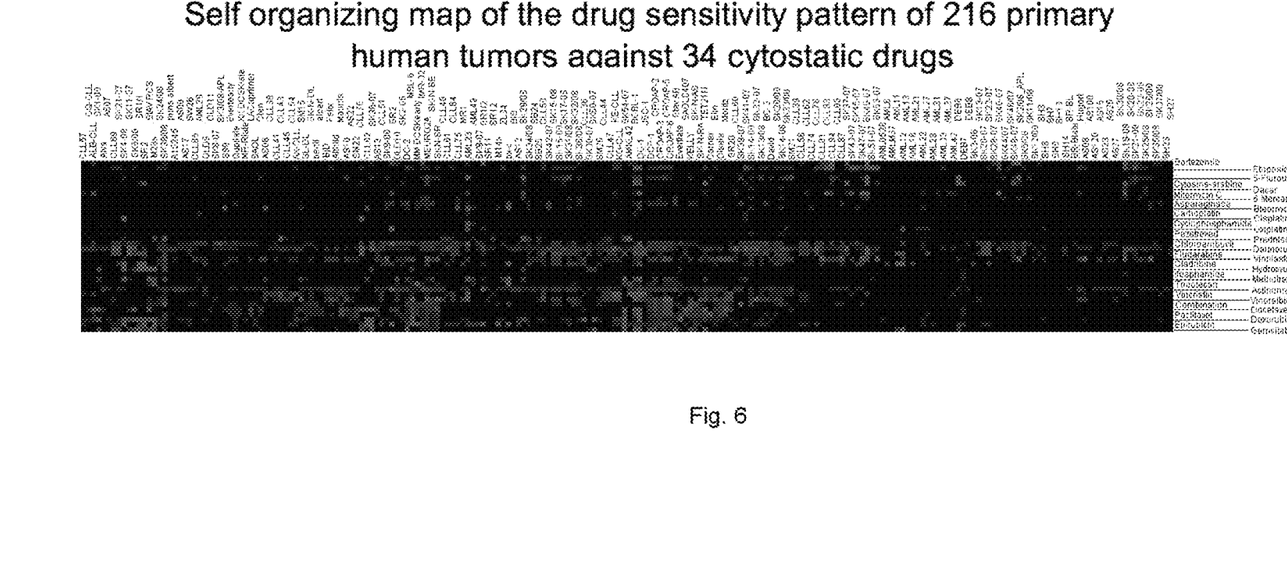
FIG. 6: Drug sensitivity pattern of 216 human primary tumor cells tested in a three days survival assay in human blood extract based medium as shown in FIG. 2. (The 5 step intensity scale of the heat map corresponds to 50% survival rate at the given drug dilution. Black: more than 50% survival at the highest drug concentration, highest intensity red less than 50% survival at the highest drug dilution).
Figure 7:
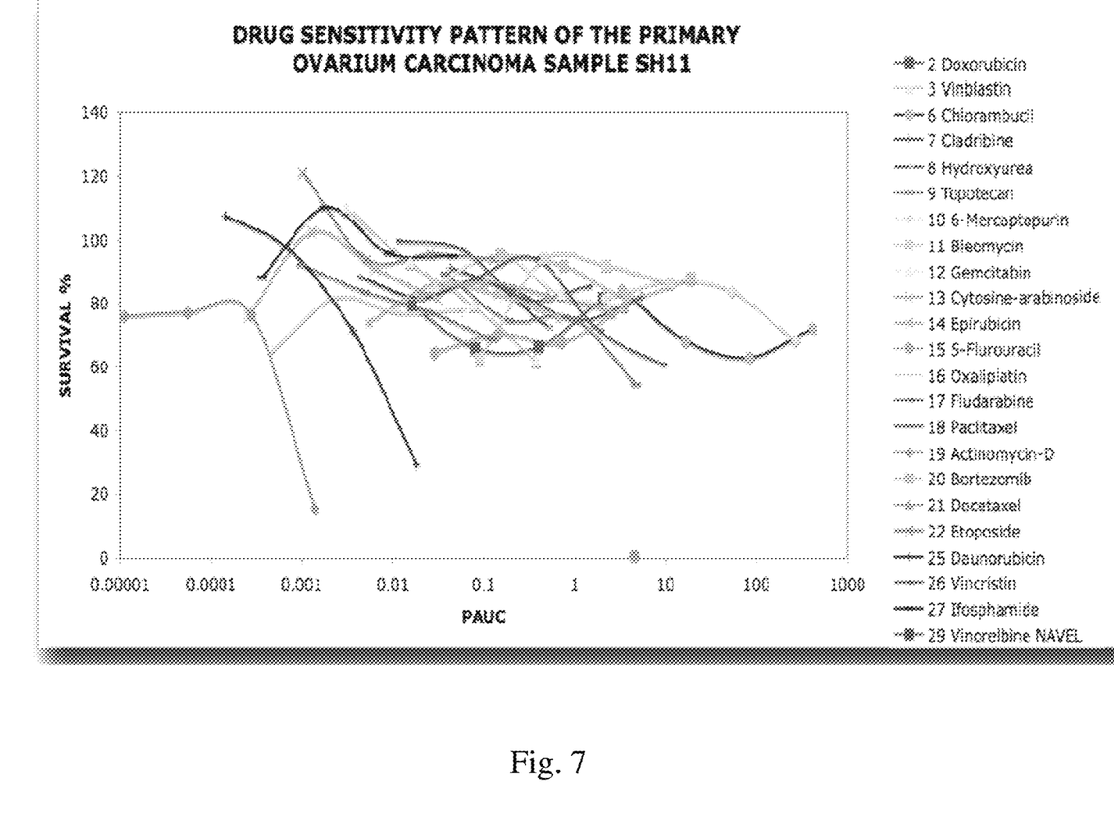
FIG. 7: Drug sensitivity pattern of highly resistant primary ovarium carcinoma cells that show significant sensitivity only for two anti cancer drugs out of 29 tested. Our blood extract based automated short term drug sensitivity assay allows the identification of potentially effective drugs even in apparently hopeless cases of late stage cancer.

For the short-term survival assay $2 \times 10^5$-$2 \times 10^6$ tumor cells (approx. 500-4000 cells per well) are diluted in 12 ml freshly thawed total blood lysate based cell culture medium. Thirty microliter samples are distributed in the wells of the pre-printed 384 well drug plate. The cells are incubated for 72 hours in an incubator at 37° C. in 5% $CO_2$ atmosphere. At the end of the incubation the cells are differentially stained with fluorescence stain mixtures that discriminate between live and dead cells (e.g. VitalDye—Biomarker, Hungary) (FIG. 2). The content of the individual wells are photographed using an automated inverted fluorescence microscope at two different excitation wavelengths [16]. The captured pictures are analyzed using digital image quantitation programs that count number of living and dead cells from binary thresholded images on a single cell level. The viability score after 3 days of incubation with the indicated drug dilution was charted as heat maps created by pairwise hierarchical clustering for different primary tumors such as lung, ovarium and breast carcinomas (FIG. 3), acute myeloid leukemias (FIG. 4), chronic lymphoid leukemias (FIG. 5). The summary drug sensitivity map of 216 primary tumors created as self-organizing map is shown in FIG. 6. These data clearly indicate that even very resistant tumors (e.g. late stage ovarium carcinoma ascites cells as shown in FIG. 7) can be sensitive for at least for a few drugs when tested in our blood extract based cell culture medium.

Total fluorescence intensity, cell size, cell surface circumference as well as morphological parameters such as circularity, feret diameter are recorded for subsequent High Content Analysis (HCA). If cell cycle distribution measurements are required the cells are subjected to a combination of permeabilization and fixation treatment, such as detergent treatment combined with aldehyde crosslinking. In practice, a mixture of formaldehyde and Nonidet P-40 is added to the fluorescently stained drug plates that yield 1 and 0.1% concentration respectively. The plates are imaged again using the parameters that were previously employed for dead cell recording. The fluorescent dye that in the first round detected the dead cells on the basis of staining the DNA in cells with compromised membrane permeability is used in the second round to measure the total DNA content in all the cells. Combination of cell cycle distribution, cell viability and detailed cell morphology data provide a valuable set of information to characterize the effect of a particular drug on the primary tumor cells. For example cell cycle stop, or the rounding up of adherent cells, provide alternative, more-subtle, toxicity endpoints on a tumor cell population where simple viability assay would show no difference.

EXAMPLE 3: COMPARISON WITH CLASSIC CELL CULTURE MEDIA (DECREASED DRUG SENSITIVITY)

Figure 8:
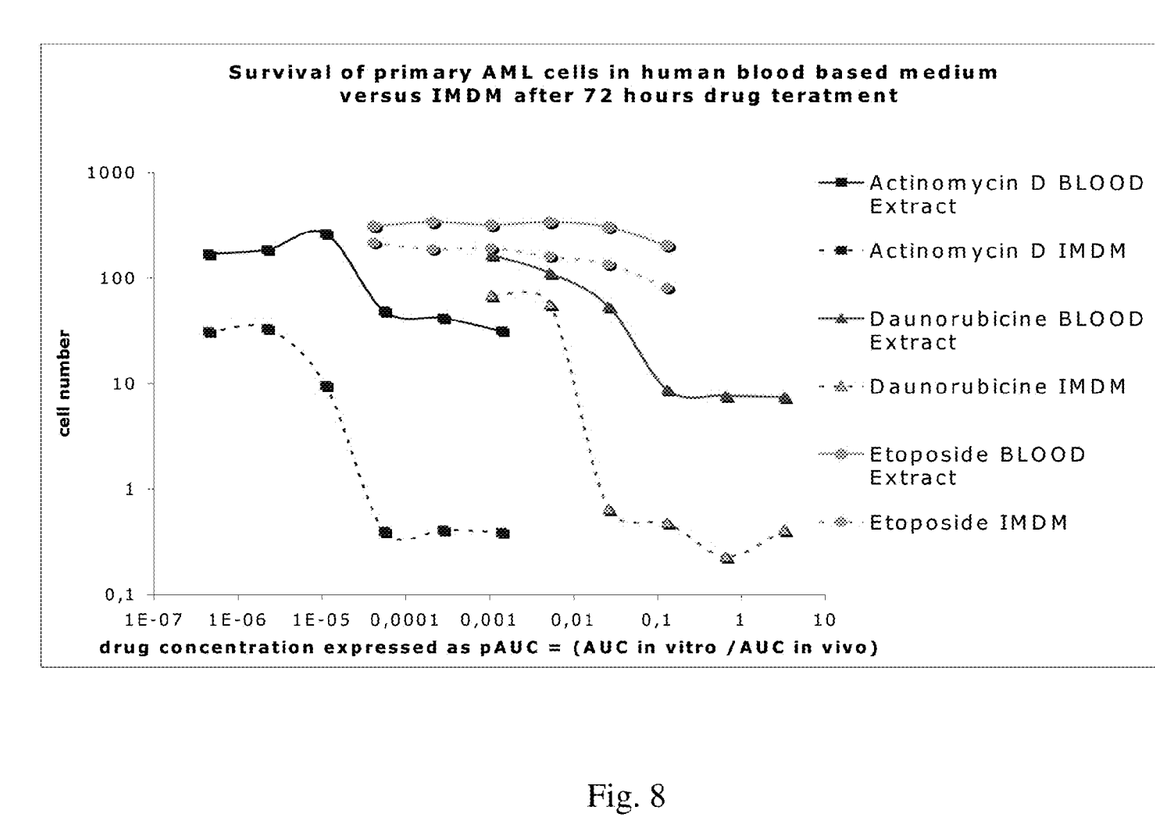
FIG. 8: The figure shows the result of a three days cell survival assay. The tumor cells were isolated from an acute myeloid leukemia (AML) patient and treated with different drugs, at different concentrations in blood extract based medium or in a traditional, rich cell culture medium—IMDM. The number of surviving cells at the end of the incubation is plotted against the relative drug concentration represented here as the proportion of in vivo/in vitro Area Under Curve*values. The value pAUC=1 represents drug concentration regularly achieved in the serum of a patient during chemotherapy. *AUC, Area Under Curve is a time dependent integration of the drug concentration curve expressed as (microgram/ml)*hours

Incubation of primary human carcinoma and leukemia cells in blood extract based and conventional medium consistently yielded higher overall survival rate and decreased sensitivity to the cytotoxic effects of different anti-cancer drugs. (FIG. 8)

EXAMPLE 4: COMPARISON OF BLOOD EXTRACTS OF HUMAN, BOVINE AND PORCINE ORIGIN

Blood extract were generated from freshly collected blood from newly slaughtered pigs or calves. The blood was collected under sterile conditions and processed as described under Example 1.

Figure 9:
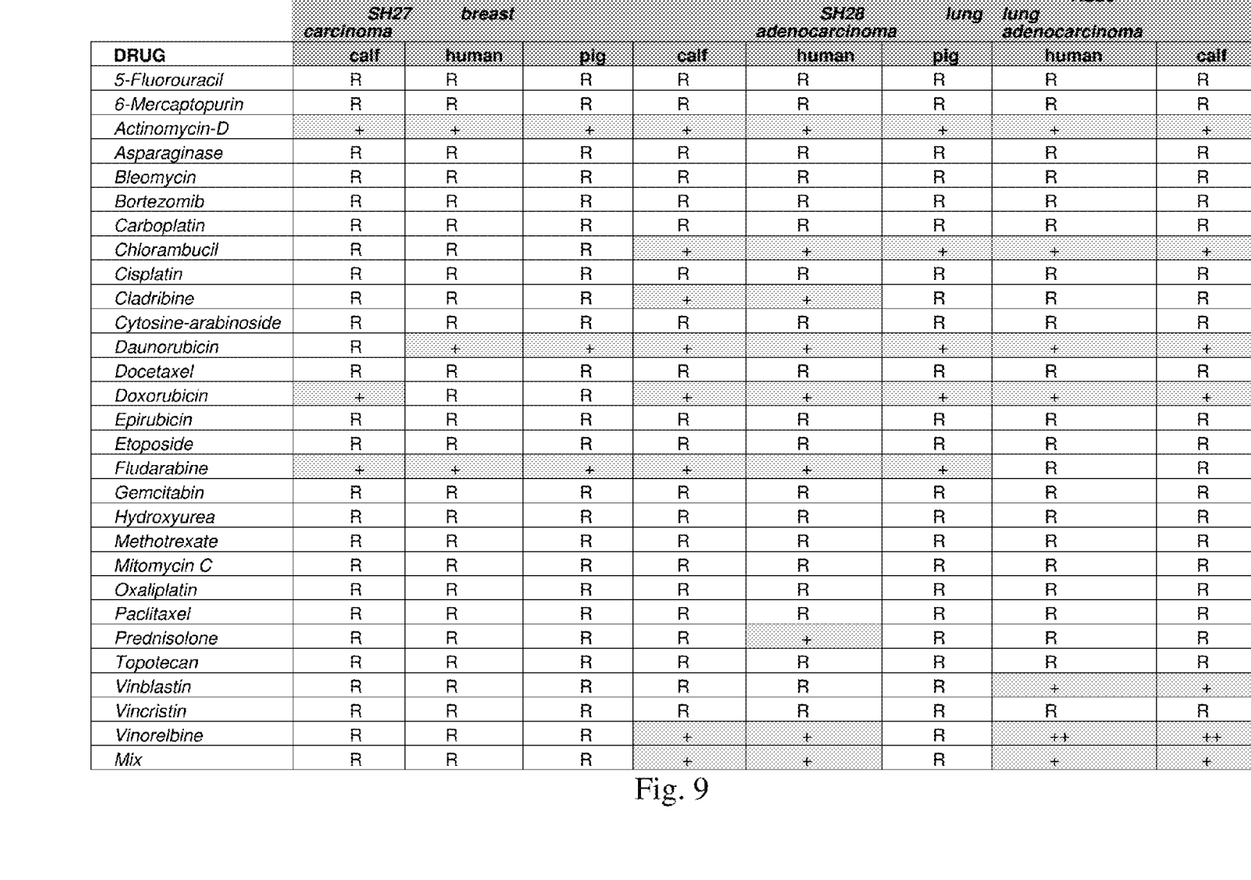
FIG. 9: Similar drug sensitivity profile of primary human carcinoma cells in blood extract based cell culture medium produced from human, bovine or porcine blood. Three days survival assay as described in FIG. 2.

Parallel assays using freshly isolated primary human carcinoma cells showed comparable drug sensitivity patterns. Primary human leukemia cells showed somewhat better survival in human blood extracts for some of the drugs. These data suggest that high throughput drug screening assays on primary human carcinoma cells form ascites or pleural effusion may be efficiently carried out using blood extract of animal origin whereas testing of drug sensitivity pattern of cells from human leukemia patients should be carried out in blood extract of human origin. (FIG. 9).

REFERENCES

1. Samson D J, Seidenfeld J, Ziegler K, Aronson N: Chemotherapy sensitivity and resistance assays: a systematic review. *J Clin Oncol* 2004, 22:3618-3630.

2. Larsson R, Nygren P: A rapid fluorometric method for semiautomated determination of cytotoxicity and cellular proliferation of human tumor cell lines in microculture. *Anticancer Res* 1989, 9:1111-1119.

3. Larsson R, Fridborg H, Kristensen J, Sundstrom C, Nygren P: In vitro testing of chemotherapeutic drug combinations in acute myelocytic leukaemia using the fluorometric microculture cytotoxicity assay (FMCA). *Br J Cancer* 1993, 67:969-974.

4. Shay J W, Wright W E: Tissue culture as a hostile environment: identifying conditions for breast cancer progression studies. *Cancer Cell* 2007, 12:100-101.

5. Nygren P, Fridborg H, Csoka K, Sundstrom C, de la Torre M, Kristensen J, Bergh J, Hagberg H, Glimelius B, Rastad J, et al.: Detection of tumor-specific cytotoxic drug activity in vitro using the fluorometric microculture cytotoxicity assay and primary cultures of tumor cells from patients. *Int J Cancer* 1994, 56:715-720.

6. Nygren P, Hagberg H, Glimelius B, Sundstrom C, Kristensen J, Christiansen I, Larsson R: In vitro drug sensitivity testing of tumor cells from patients with non-Hodgkin's lymphoma using the fluorometric microculture cytotoxicity assay. *Ann Oncol* 1994, 5 Suppl 1:127-131.

7. Villman K, Blomqvist C, Larsson R, Nygren P: Predictive value of in vitro assessment of cytotoxic drug activity in advanced breast cancer. *Anticancer Drugs* 2005, 16:609-615.

8. Nagourney R A: Ex vivo programmed cell death and the prediction of response to chemotherapy. *Curr Treat Options Oncol* 2006, 7:103-110.

9. Arosa F A, Pereira C F, Fonseca A M: Red blood cells as modulators of T cell growth and survival. *Curr Pharm Des* 2004, 10:191-201.

10. Fonseca A M, Pereira C F, Porto G, Arosa F A: Red blood cells upregulate cytoprotective proteins and the labile iron pool in dividing human T cells despite a reduction in oxidative stress. *Free Radic Biol Med* 2003, 35:1404-1416.

11. Fonseca A M, Pereira C F, Porto G, Arosa F A: Red blood cells promote survival and cell cycle progression of human peripheral blood T cells independently of CD58/LFA-3 and heme compounds. *Cell Immunol* 2003, 224:17-28.

12. Fonseca A M, Porto G, Uchida K, Arosa F A: Red blood cells inhibit activation-induced cell death and oxidative stress in human peripheral blood T lymphocytes. *Blood* 2001, 97:3152-3160.

13. Porto B, Fonseca A M, Godinho I, Arosa F A, Porto G: Human red blood cells have an enhancing effect on the relative expansion of CD8+ T lymphocytes in vitro. *Cell Prolif* 2001, 34:359-367.

14. Markasz L, Stuber G, Flaberg E, Jernberg A G, Eksborg S, Olah E, Skribek H, Szekely L: Cytotoxic drug sensitivity of Epstein-Barr virus transformed lymphoblastoid B-cells. *BMC Cancer* 2006, 6:265.

15. Markasz L, Stuber G, Vanherberghen B, Flaberg E, Olah E, Carbone E, Eksborg S, Klein E, Skribek H, Szekely L: Effect of frequently used chemotherapeutic drugs on the cytotoxic activity of human natural killer cells. *Mol Cancer Ther* 2007, 6:644-654.

16. Flaberg E, Sabelstrom P, Strandh C, Szekely L: Extended Field Laser Confocal Microscopy (EFLCM): combining automated Gigapixel image capture with in silico virtual microscopy. *BMC Med Imaging* 2008, 8:13.

The invention claimed is:

1. A method for culturing human cells, said method comprising
preparing an anti-coagulated total blood material that lacks the membrane fraction of red blood cells and has a hemoglobin level from 8 to 16 g/dl by
(a) obtaining mammalian blood having an extracellular fraction, as starting material;
(b) adding an anticoagulant to the mammalian blood thereby providing anti-coagulated mammalian blood;
(c) mechanically disrupting the cells present in the anti-coagulated mammalian blood;
(d) removing insoluble remnants of the disrupted cells to produce a particle-free extract;
(e) modifying the ion content of the particle-free extract to match the extracellular fraction of the starting material or to be similar to that of a medium selected form the group consisting of Dulbecco's Modified Eagle's Medium (DMEM), Roswell Park Memorial Institute (RPMI) medium and Isocove's Modified Dulbecco's Medium (IMDM), to produce a cell culture medium; and
(f) culturing the human cells in the cell culture medium.

2. The method according to claim 1 wherein the mechanical disruption of the cells is achieved by freezing the total blood or by ultrasound, electric blade homogenizer or French press.

3. The method according to claim 1, wherein removal of the insoluble remnants of the disrupted cells is achieved by ultracentrifugation or mechanical filtration.

4. The method according to claim 1, wherein the composition of the nutrients with a molecular weight of less than 3000 Dalton in the cell culture medium is adjusted by dialysis against a medium selected form the group consisting of DMEM, RPMI medium and IMDM.

5. The method according to claim 1, wherein the reducing capacity of the cell culture medium is restored by addition of reduced glutathione.

6. The method of claim 1, wherein the blood is of human origin.

7. The method of claim 1, further comprising carrying out high throughput microscopic imaging on the cell culture medium.

8. The method of claim 1, wherein the growth and survival factor flora of the starting material is preserved in the cell culture medium.

9. The method of claim 1, wherein the anticoagulant is heparin.

10. The method of claim 1, wherein the disrupting of the cells achieves an even disruption of cell membranes of the cells.

11. The method of claim 1, wherein the cell culture medium contains all macromolecular components of the mammalian blood.

12. The method according to claim 1 wherein the mechanical disruption of the cells is achieved by freezing the anti-coagulated mammalian blood.

13. The method of claim 1, wherein the ion content of the particle-free extract is restored to match that of the extracellular fraction of the starting material.

14. A method for culturing human cells, said method comprising
preparing an anti-coagulated total blood material that lacks the membrane fraction of red blood cells by
(a) obtaining mammalian blood having an extracellular fraction, as starting material;

(b) adding an anticoagulant to the mammalian blood thereby providing anti-coagulated mammalian blood;
(c) lysing the cells present in the anti-coagulated mammalian blood to produce lysed anti-coagulated mammalian blood;
(d) removing insoluble remnants of the lysed cells from the lysed anti-coagulated mammalian blood; and
(e) modifying the ion content of the lysed anti-coagulated mammalian blood to match that of the extracellular fraction of the starting material or to be similar to that of a medium selected form the group consisting of Dulbecco's Modified Eagle's Medium (DMEM), Roswell Park Memorial Institute (RPMI) medium and Isocove's Modified Dulbecco's Medium (IMDM),
to produce a cell culture medium having a hemoglobin level from 8 to 16 g/d; and
culturing the human cells in the cell culture medium.

15. The method according to claim 14, wherein removal of the insoluble remnants of the lysed cells is achieved by ultracentrifugation or mechanical filtration.

16. The method according to claim 14 wherein the lysing of the cells is achieved by freezing the anti-coagulated mammalian blood.

* * * * *